(12) United States Patent
Krieg-Kowald et al.

(10) Patent No.: US 7,688,524 B2
(45) Date of Patent: Mar. 30, 2010

(54) LASER PROTECTIVE EYEWEAR HAVING IMPROVED GLARE PROTECTION

(75) Inventors: Marianne Krieg-Kowald, Barrington, RI (US); Mark McLear, Lincoln, RI (US)

(73) Assignee: Sperian Eye & Face Protection, Inc., Smithfield, RI (US)

( * ) Notice: Subject to any disclaimer, the term of this patent is extended or adjusted under 35 U.S.C. 154(b) by 89 days.

(21) Appl. No.: 12/108,557

(22) Filed: Apr. 24, 2008

(65) Prior Publication Data

US 2009/0268157 A1 Oct. 29, 2009

(51) Int. Cl.
*G02B 5/20* (2006.01)

(52) U.S. Cl. .................. 359/722; 359/350; 351/165

(58) Field of Classification Search ........... 351/162, 351/163, 165; 359/722, 723, 577–590
See application file for complete search history.

(56) References Cited

U.S. PATENT DOCUMENTS

| | | | | |
|---|---|---|---|---|
| 5,059,500 A | * | 10/1991 | Needham et al. | 430/7 |
| 5,140,396 A | * | 8/1992 | Needham et al. | 257/294 |
| 6,229,252 B1 | * | 5/2001 | Teng et al. | 313/112 |
| 6,680,009 B2 | * | 1/2004 | Harada et al. | 252/587 |
| 2008/0043200 A1 | * | 2/2008 | Ishak | 351/163 |

* cited by examiner

*Primary Examiner*—Darryl J Collins
(74) *Attorney, Agent, or Firm*—Barlow, Josephs & Holmes, Ltd.

(57) ABSTRACT

A molded optical filter is provided having effective filtering of energy emissions at an optical density (OD) of greater than 4 in three energy emission bands corresponding to the wavelengths of laser emissions while preserving the wearer's ability to differentiate and recognize colors and having a pleasing overall color. The selective optical filter is a moldable polymer filter that has three dyes therein to produce sharp notch filtering ranges at about 530 nm, 700 nm and 1060 nm and a fourth color balance dye therein to adjust the overall color of the filter making it more pleasing and desirable to the wearer.

13 Claims, 5 Drawing Sheets

Filter # 108

VLT = 30-35%   PRIOR ART

Filter # 111

VLT = 10-14%

LASER PROTECTIVE EYEWEAR HAVING IMPROVED GLARE PROTECTION

BACKGROUND OF THE INVENTION

The present invention relates generally to optical safety filters. More specifically, the present invention relates to optical safety filters that provide laser protection across a plurality of narrowly selected wavelength ranges corresponding to laser emissions, while also including a color-balancing component that enhances the color rendering performance of the filter.

In a number of commercial and military fields there is a growing awareness that certain wavelengths of energy emissions are harmful to the eye. Generally, such energy emissions, in the form of a laser emission, are grouped at or around three wavelengths corresponding to approximately 400-1400 nm. For example, energy emitted from a laser operating in one of these wavelength ranges can cause both temporary and permanent blindness and can be disorienting to those people that have been exposed. The adverse effects of energy emissions having wavelengths within these wavelength regions are only recently beginning to be fully recognized as applications that utilize such energy emissions are more frequently employed. For example, there are a number of optical communication protocols that utilize lasers tuned to these wavelengths for the transmission of data as well as a number of military applications that employ infra-red and near infra-red laser energy emissions at these wavelengths in connection with the sighting of weapons and target acquisition. As the environments in which the use of such energy emissions increases, the potential for accidental exposure to such emissions also greatly increases.

In the past, to avoid accidental exposure to infra-red and visible laser emissions, people have attempted to protect their eyes through the use of nonselective filters that simply include a broad wavelength dark filter that screens out the potential for exposure to harmful emission levels. In this regard, however, the broadband filters reduce the magnitude of the exposure over a wider range than screening out the harmful wavelengths of energy. As a result, with only a few exceptions, such filters have generally been directed toward the reduction in intensity of the light transmitted, rather than to the filtering of any particular wavelength or group of wavelengths.

The problem with such a prior art approach is that the nonselective reduction in overall light transitivity generally impacts the visual acuity of the wearer making the use of such filtering difficult if not impossible to implement due to the severe limitations imposed on the visibility of the wearer. One key area that further limits the wearability of such generalized filters is traffic signal recognition. To meet the standards required for use as sunglasses, the wearer must be able to differentiate between red and green traffic signals. Often broad filters directed at screening the above laser energy emissions also result in severely limiting the wearer's ability to differentiate between red and green objects making traffic identification difficult if not impossible.

Another prior art approach involved in laser filtering related to the use of specialty lenses. The difficulty with such lenses is that they typically have a limited range of properties, because they are made of glass or high impact polymers such as polycarbonate, thereby requiring that the additives used to modify the transmissivity must be compatible with the high temperatures required in making the glass or molding of the polymer material. The range of substances that are available that are both compatible with the high molding temperatures and capable of imparting the desired filtering properties is very narrow and generally does not provide the versatility typically encountered with organic dyestuffs that are normally utilized for narrow wavelength filtering. An example of such a prior art filter is illustrated in the performance graph at FIG. 1. The curve illustrates a prior art optical filter tailored for filtering energy in the range of approximately 755 nm-1064 nm. As can be seen, the filter provides a filtering performance curve that exhibits filtering characteristics on the order of 5 optical density (OD) between the wavelengths of about 755 nm to about 1064 nm. In addition, however, the filter still exhibits filtering on the order of 2-3 OD for wavelengths as low as 700 nm and as high as 1080 nm. Since transmissivity is the inverse of OD to the base 10, this translates to a transmissivity of almost zero in the target filtering range of 755 nm-1064 nm with a visible light transmission (VLT) across the remaining spectrum of only around 30-35%. As can be seen, the results indicate a relatively low performance filter with a limited VLT value.

Should the above approach be taken to create a filter to cover all three of the identified energy emission ranges, a lens is produced that exhibits a very undesirable color. Not only is this undesirable from a commercial standpoint, it further encounters the problem that the filter does not allow the wearer to differentiate well between reds and greens. Finally, such a lens has a low light transmissivity because the overlap of the three broad filtering ranges needed to cover the target energy covers almost the entire visible spectrum.

As a result there is a need for an optical filter that blocks narrow bands of energy emissions corresponding laser energy emission while preserving the wearer's ability to differentiate between reds and greens. There is a further need for an optical filter that is molded from a polymer and includes dyes that filter laser energy emissions while having a pleasing overall color and while also preserving the wear's ability to differentiate between colors.

BRIEF SUMMARY OF THE INVENTION

In this regard, the present invention provides for a molded optical filter that provides effective filtering of laser emissions while preserving the wearer's ability to differentiate and recognize colors and providing a pleasing overall color as compared to the prior art. The present invention is directed generally to a selective optical filter that has multiple dyes therein to produce sharp notch filtering ranges at about blue, green, red and infrared light spectrum and additional dyes for color balancing to adjust the overall color of the filter making it more pleasing and desirable to the wearer. In other words, the optical filter of the present invention effectively reduces transmission of laser energy in the selected ranges while preserving the wearer's ability to differentiate colors and improving the overall color of the filter itself thereby making the filter more desirable to the wearer.

It is therefore an object of the present invention to provide a filtering panel that filters laser energy emissions in the blue, green, red and infrared while also being suitable for use as sunglasses. It is a further object of the present invention to provide an optical filter that filters laser energy emissions at about blue, green, red and IR while also including a color balance dye that improves the overall color of the optical filter itself. It is still a further object of the present invention to provide a molded optical filter that includes dyes that filter energy emissions to a non-hazardous level from laser while also including a color balance dye(s) to improve the overall color of the optical filter itself. These together with other objects of the invention, along with various features of novelty that characterize the invention, are pointed out with particularity in the claims annexed hereto and forming a part of this disclosure. For a better understanding of the invention, its operating advantages and the specific objects attained by its uses, reference should be had to the accompanying descriptive matter in which there is described several embodiments of the invention.

BRIEF DESCRIPTION OF THE DRAWINGS

In the drawings which illustrate the best mode presently contemplated for carrying out the present invention.

DETAILED DESCRIPTION OF THE INVENTION

The best mode for carrying out the present invention is illustrated herein in the context of an optical filter that preferably includes dyes directed at filtering energy emissions in and about the wavelength ranges of blue, green, red and IR and more particularly in the range of traffic lights and lasers in the 530, 600-700 and military lasers while also including a color balancing dye(s) to improve the overall performance and aesthetic appeal of the optical filter. As was stated above, as applications that employ infrared and/or laser energy increase, the need to protect people against accidental exposure also greatly increases. For this reason, the present invention provides an optical filter capable of filtering energy emissions in the wavelength ranges that cover various laser energy emissions while also providing a lens that is color balanced in a manner that preserves a wearer's ability to distinguish colors and has a more pleasing overall color as compared to the prior art.

In the context of this invention, various optical terms are used to describe the optical filter. To facilitate the understanding of the invention, these terms are initially defined as follows:

Lens: an ophthalmic lens that provides refractive correction or a lens that provides no refractive correction also known as a "plano lens".

Visible light spectrum: energy emissions having a wavelength of between approximately 400 nm and 780 nm.

Visible light transmission (VLT): the percentage of light in the visible spectrum range that the filter of the present invention allows to pass through to the eyes of the user.

Blocking: a measure of the percentage of light that is either reflected by the surface or surface coatings or absorbed by the dye or plastic of the lens.

Substantially blocking: the point at which the filter of the present invention blocks over 99 percent of the incident radiation or transmits less than one-percent (1.0%) of the incident radiation at each and every wavelength within the defined range.

Figure 1:
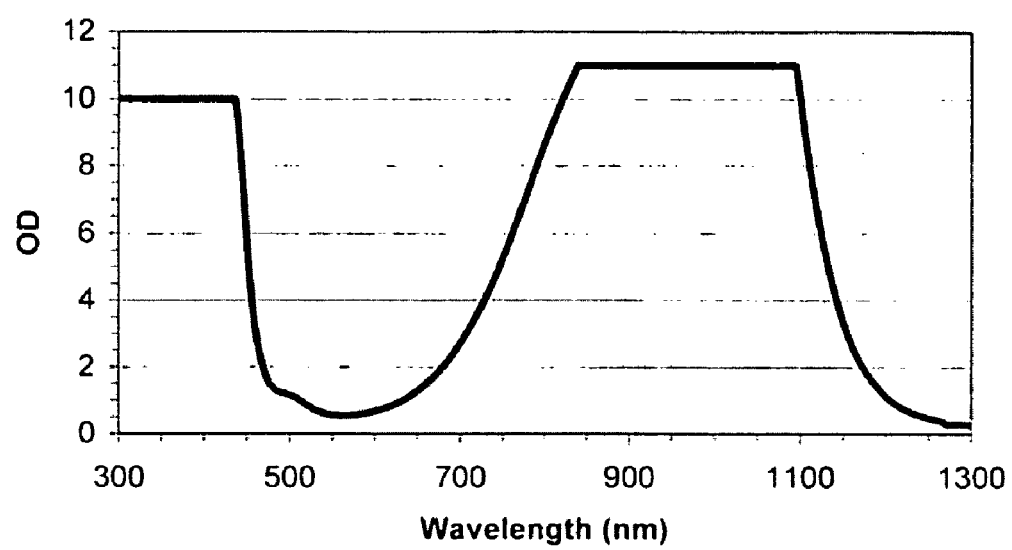
FIG. 1 is a graph depicting the filtering characteristics of a prior art optical filter.
Figure 2:
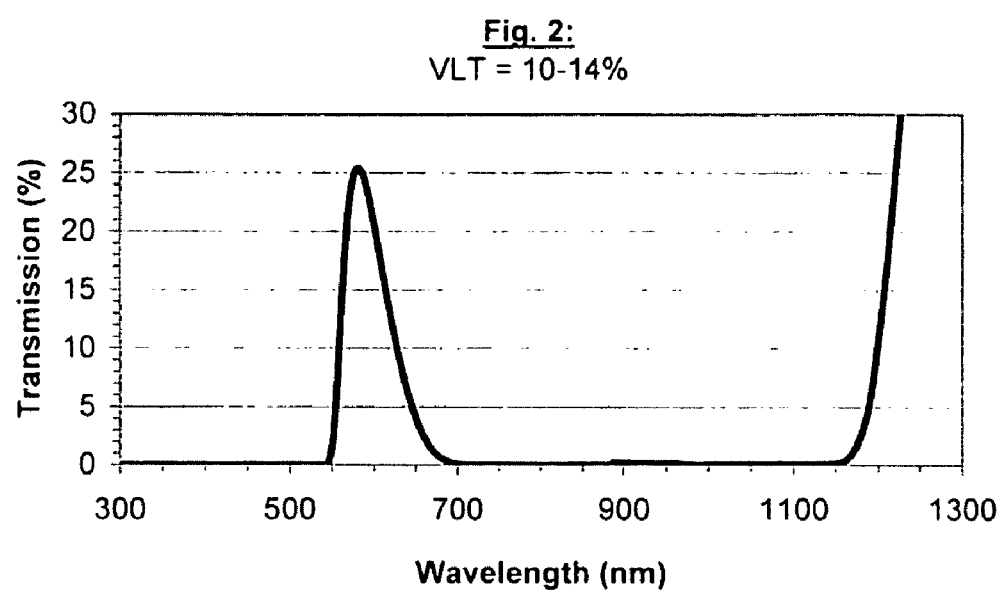
FIG. 2 is a graph depicting the filtering characteristics of a filter with dyes covering the blue, green, red and IR wavelengths.

Turning now to FIG. 2, an optical filter directed at filtering the relevant wavelengths. The optical filter can be seen to screen or substantially block all of the energy associated with emissions in the ranges of approximately 190-530 nm, 700 nm through 1060 nm. As was stated above however, such a filtering characteristic as is depicted in FIG. 2 has two distinct drawbacks in that it produces an optical filter having an unattractive color while also greatly impairing the wearer's ability to distinguish colors such as those in traffic signals. To overcome this problem, the present invention includes dyes that provide selective screening of hazardous laser radiation and produce color-balancing effects. The combination of these dyes has two effects. It provides protection from hazardous laser radiation while at the same time providing glare protection and traffic color signal recognition associated with typically sunglasses.

Figure 3:
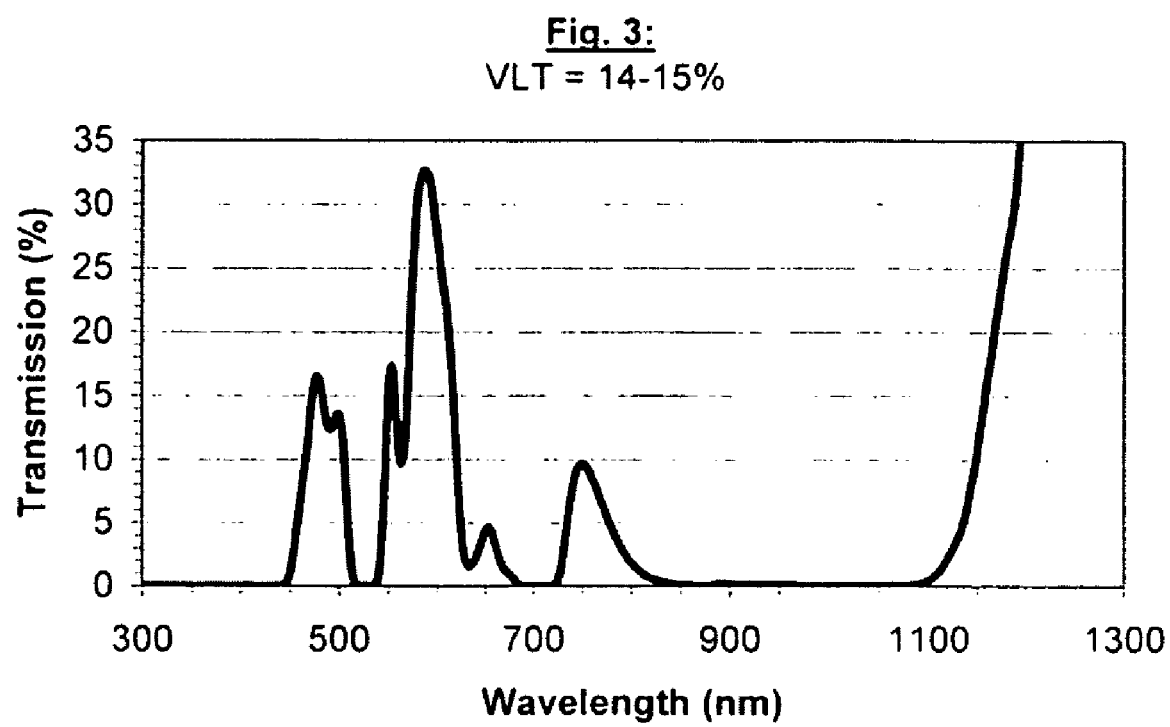
FIG. 3 is a graph depicting the filtering characteristics of a filter in accordance with the teachings of the present invention.
Figure 4:
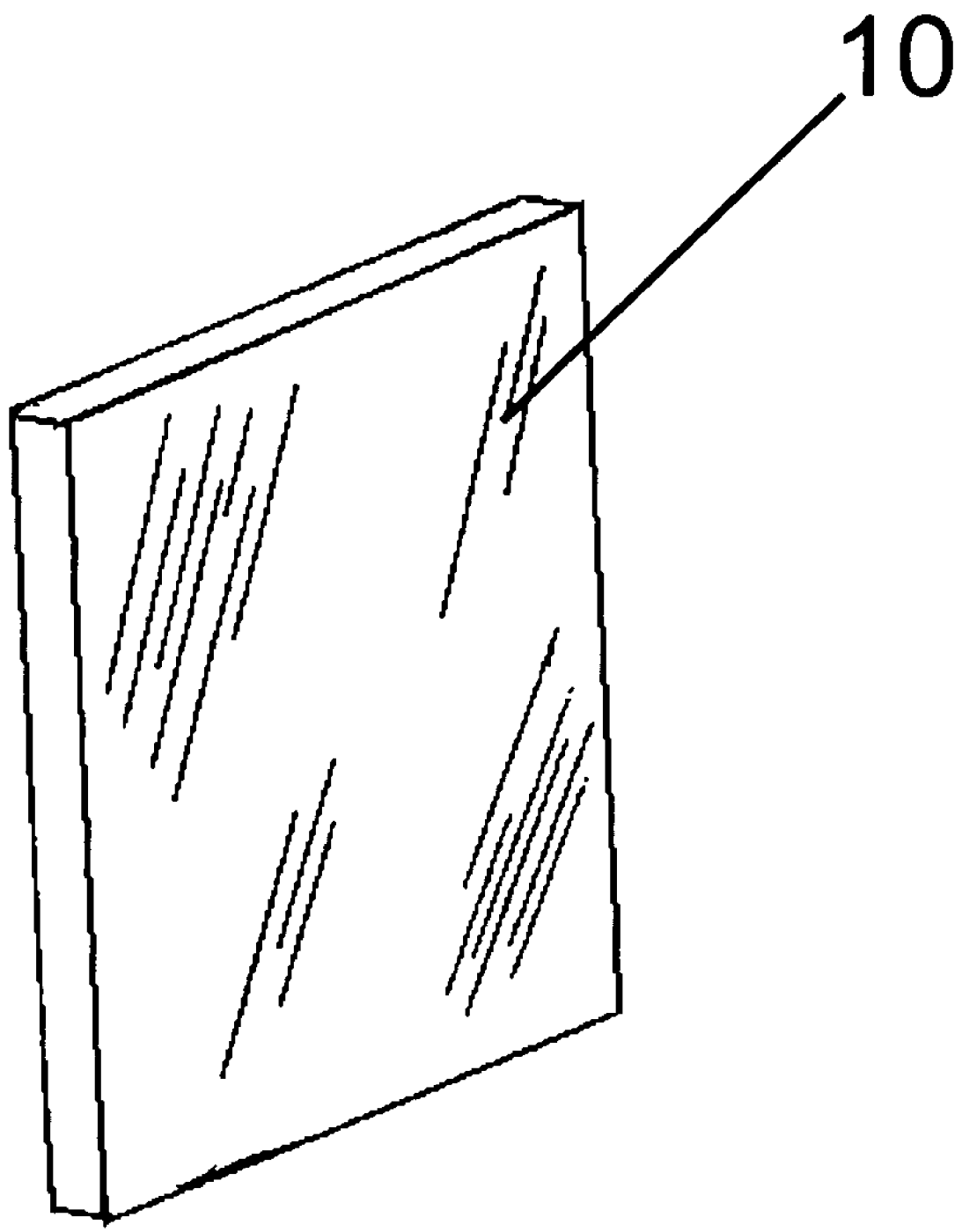
FIG. 4 depicts a filter plate or window formed in accordance with the teachings of the present invention.
Figure 5:
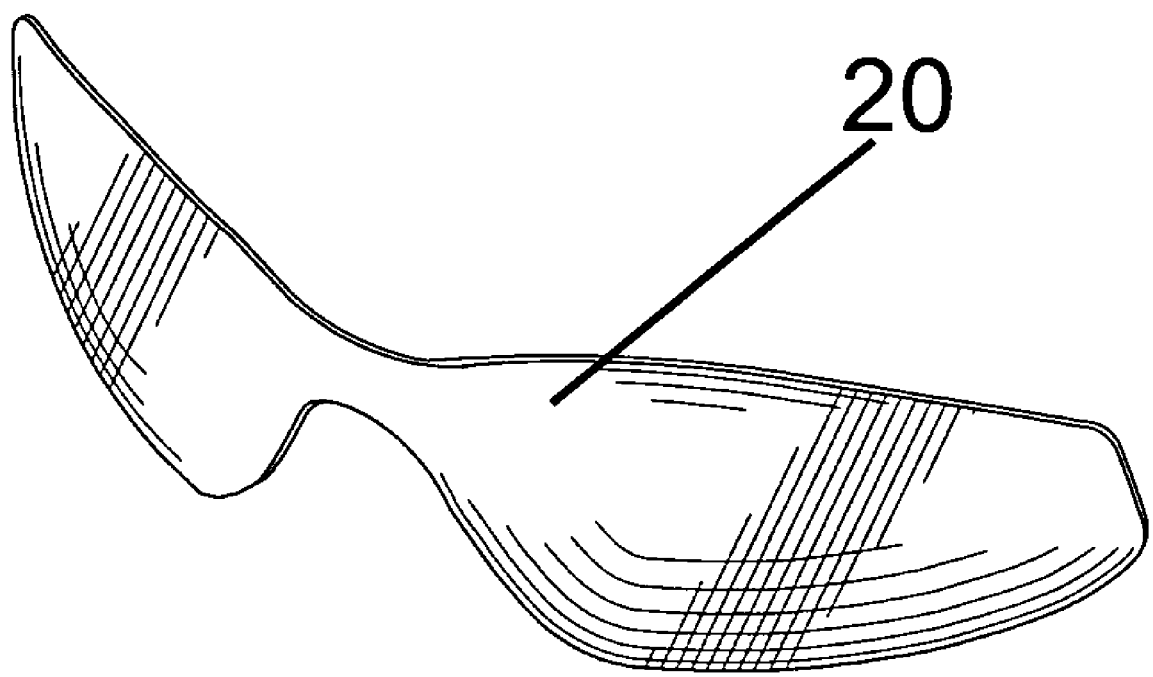
FIG. 5 depicts a lens blank or eyewear formed in accordance with the teachings of the present invention.

As can be seen in FIG. 3, the present invention also provides for an optical filter that includes dyes for selectively screening out hazardous laser radiation and color balancing dyes. The combination of these dyes allows you to be protected from laser radiation and also provide glare protection while allowing you to see traffic signals. The optical filter of the present invention is intended to be formed as a polymer filter and may take the form of a filter panel, a lens blank, safety eyewear or a window. The optical filter is designed to be utilized in any environment where the potential for exposure to laser energy emissions exists due to the fact that such energy emissions are deleterious to the eyes. The optical filter of the present invention is preferably formed from a transparent polymer matrix material that is suitable for making ophthalmic quality lenses. Preferably, the optical filter of the present invention is formed using a polycarbonate, nylon or acrylic. It is further preferred that the particular polymer selected be well suited to the application in which the finished optical filter will be employed. For example, lens blanks 10 as are depicted in FIG. 4 are typically formed using a polycarbonate while windows 20 as are depicted in FIG. 5 are formed using acrylic.

In all cases, despite the application, the optical filter of the present invention provides an effective filter barrier to the targeted laser energy emissions thereby preventing damage to the user's eyes while providing glare protection and traffic signal recognition. As can be seen in FIG. 3, dyes are incorporated into the lens material prior to the molding of the lens. The dyes have characteristics that allow the lens to transmit a greater amount of the of the visible light spectrum adjacent the filtering ranges while blocking more than 99% of all energy emissions having wavelengths that fall in the of relevant hazardous laser wavelengths ranges. This further allows color balancing to shift the overall color of the lens and allow the optical filter to meet the standards required of sunglasses while not becoming too dark to be widely usable.

In forming the optical filter of the present invention, two different methods may be employed. First, polymer molding feedstock in the form of polymer pellets is provided that is then mixed with the dye material typically in the form of a powder. The pellets and dye are mixed by tumbling the materials together. The pellet and dye mixture is then introduced into the feed hopper of an extrusion-molding machine wherein the mixture is melted and homogenized in the barrel of the molding machine. Finally, the molten material is extruded either through an extrusion die or into a mold to form the finished optical filter. Alternately, in a second method, the molten material may be extruded using a small diameter extrusion die and pelletized to form a homogenized, dyed polymer feed stock. These pellets are then utilized in subsequent molding operations wherein the pellets are remelted and further extruded or injected into a mold cavity to form the finished optical filter.

It can therefore be seen that the present invention provides a novel optical filter having the ability to substantially block energy emissions from hazardous laser radiation, while preserving the ability to distinguish between colors associated with traffic signals and provide glare reduction typically found in sunglasses. For these reasons, the instant invention is believed to represent a significant advancement in the art, which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. An optical filter comprising:
   a transparent filter blank;
   a first dye dispersed within said filter blank, said first dye substantially blocking 99 percent of energy emissions corresponding to a first laser wavelength;
   a second dye dispersed within said filter blank, said second dye substantially blocking 99 percent of energy emissions corresponding to a second laser wavelength;
   a third dye dispersed within said filter blank, said third dye substantially blocking 99 percent of energy emissions corresponding to a third laser wavelength; and
   a color balancing dye dispersed within said filter blank, said color balancing dye shifting a color of said filter blank containing said first second and third dyes from a green color to a brown color.

2. The optical filter of claim 1, wherein said transparent filter blank is formed from a transparent polymer base matrix material.

3. The optical filter of claim 2, wherein said polymer base matrix material is selected from the group consisting of: polycarbonate, nylon and acrylic.

4. The optical filter of claim 2, wherein said first, second, third and color balancing dyes are uniformly dispersed throughout said base polymer matrix material.

5. The optical filter of claim 1, wherein said optical filter is selected from the group consisting of: lens blanks, lenses for eyewear, windows and filtering plates.

6. The optical filter of claim 1, wherein said first, second and third dyes are selected to have a filtering wavelength to filter said first, second and third laser emissions yet preserve a wearer's ability to distinguish colors.

7. The optical filter of claim 6, wherein said optical filter is a lens for sunglasses and said first, second and third dyes are selected to preserve said wearer's ability to distinguish between red and green traffic signals.

8. An optical filter comprising:
   a moldable transparent polymer base matrix material;
   a first sharp cut-on dye having an optical density of greater than 4 in a wavelength range of about 530 nm±20 nm dispersed within said base polymer matrix;
   a second sharp cut-on dye having an optical density of greater than 4 in a wavelength range of about 700 nm±20 m dispersed within said base polymer matrix;
   a third sharp cut-on dye having an optical density of greater than 4 in a wavelength range of about 1060 nm±20 nm dispersed within said base polymer matrix; and
   a color balancing dye dispersed within said base polymer matrix, said color balancing dye shifting a color of said optical filter containing said first second and third dyes from a green color to a brown color.

9. The optical filter of claim 8, wherein said polymer base matrix material is selected from the group consisting of: polycarbonate, nylon and acrylic.

10. The optical filter of claim 8, wherein said first, second, third and color balancing dyes are uniformly dispersed throughout said base polymer matrix material.

11. The optical filter of claim 8, wherein said optical filter is selected from the group consisting of: lens blanks, lenses for eyewear, windows and filtering plates.

12. The optical filter of claim 8, wherein said first, second and third dyes are selected to preserve a wearer's ability to distinguish colors.

13. The optical filter of claim 12, wherein said optical filter is a lens for sunglasses and said first, second and third dyes are selected to preserve said wearer's ability to distinguish between red and green traffic signals.

* * * * *